United States Patent [19]

Heinze

[11] Patent Number: 5,500,006
[45] Date of Patent: Mar. 19, 1996

[54] ARRANGEMENT, PARTICULARLY A HEART PACEMARKER, FOR ACQUIRING A MEASUREMENT PARAMETER OF THE HEART ACTIVITY

[75] Inventor: Roland Heinze, Munich, Germany

[73] Assignee: Pacesetter AB, Solna, Sweden

[21] Appl. No.: 39,190

[22] PCT Filed: Oct. 4, 1991

[86] PCT No.: PCT/EP91/01897

§ 371 Date: Jun. 4, 1993

§ 102(e) Date: Jun. 4, 1993

[87] PCT Pub. No.: WO92/05836

PCT Pub. Date: Apr. 16, 1992

[30] Foreign Application Priority Data

Oct. 4, 1990 [DE] Germany ............. 40 31 450.2

[51] Int. Cl.[6] .................................. A61N 1/365
[52] U.S. Cl. ........................................... 607/24
[58] Field of Search .................. 607/17, 19, 20, 607/24, 22

[56] References Cited

U.S. PATENT DOCUMENTS

| 4,114,627 | 9/1978 | Lewyn et al. . |
| 4,535,774 | 8/1985 | Olson . |
| 4,802,481 | 2/1989 | Schroeppel . |
| 4,817,606 | 4/1989 | Lekholm . |
| 4,856,521 | 8/1989 | Irnich . |
| 4,930,517 | 6/1990 | Cohen et al. . |

FOREIGN PATENT DOCUMENTS

| 0059868 | 9/1982 | European Pat. Off. ......... A61N 1/36 |
| 0140472 | 5/1985 | European Pat. Off. ......... A61N 1/36 |
| 0165566 | 12/1985 | European Pat. Off. ....... A61N 1/365 |
| 0194224 | 9/1986 | European Pat. Off. ....... A61N 1/365 |
| 0219943 | 4/1987 | European Pat. Off. ....... A61N 1/365 |
| 0237767 | 9/1987 | European Pat. Off. ....... A61N 1/365 |
| 0255899 | 2/1988 | European Pat. Off. ....... A61N 1/365 |
| 0317985 | 5/1989 | European Pat. Off. ....... A61N 1/365 |
| 0327292 | 8/1989 | European Pat. Off. ....... A61N 1/365 |
| 3533597A1 | 4/1987 | Germany .................... A61N 1/36 |
| 3715823A1 | 12/1987 | Germany .................... A61B 5/02 |
| 3732699A1 | 4/1988 | Germany .................... A61N 1/36 |
| 3905323A1 | 12/1989 | Germany .................... A61N 1/365 |
| 494028 | 9/1970 | Switzerland ................ A61N 31/00 |
| 587052 | 4/1977 | Switzerland ................ A61H 31/00 |
| WO89/06999 | 8/1989 | WIPO ..................... A61N 1/365 |
| WO90/09757 | 9/1990 | WIPO ..................... A61B 5/0245 |

OTHER PUBLICATIONS

Herz/Kreisl. 18 (Nov. 1980), E. Alt et al "Therapie mit Frequenzadaptiven Herzschrittmachern", pp. 556–564.

Biomedizinische Technik, May, 1988, G. Boheim et al "Frequenzadaption eines kunstlichen Herzschrittmachers uber einen Volumenregelkreis", pp. 100–105.

Biomed Technik, vol. 34 (1989), M. Schaldach, "PEP–gesteuerter Herzschrittmacher" (Pacemaker with PEP–Controlled Rate Adaptation), pp. 177–184.

Primary Examiner—William E. Kamm
Assistant Examiner—Scott M. Getzow
Attorney, Agent, or Firm—Hill, Steadman & Simpson

[57] ABSTRACT

An arrangement, in particular a heart pacemaker, has a measuring device for recording a heart activity measurement parameter. In order to record the measurement parameter in such a way that it is rid of disturbing signals, and can thus be used to evaluate the physiological functions of the heart pacemaker, the arrangement contains switching means which evaluate the signal curve of a measurement parameter during a heart cycle (n+1) as a function of the frequency (f) or duration ($t_S$) of the previous heart cycle (n).

6 Claims, 3 Drawing Sheets

ARRANGEMENT, PARTICULARLY A HEART PACEMARKER, FOR ACQUIRING A MEASUREMENT PARAMETER OF THE HEART ACTIVITY

BACKGROUND OF THE INVENTION

The invention is directed to an arrangement, particularly a heart pacemaker, comprising a measuring means for acquiring a measurement parameter of heart activity.

International Patent Application WO 89/06990 discloses how it is possible to implement a hemodynamic optimization of the frequency control with the assistance of a periodic change of the stimulation frequency, the simultaneous acquisition of a measurement parameter proportional to the cardiac minute output, and appropriate calculating methods. What is critical in this measuring method, however, is that the frequency changes occur over time intervals that not only result in a reaction of the heart muscle, but also result in a reaction of the entire cardiovascular control system; and that this reaction is the prerequisite for desired optimization of the frequency range of the stimulation frequency.

In a heart pacemaker disclosed by EP-A00 255 899, the stimulation frequency is regulated dependent on the atrioventricular transition time as a stress-dependent reference variable input. In addition to characteristics control, a hemodynamic optimum control is thereby also provided in that the stimulation frequency is increased or reduced given a constant degree of physical stress until the measured atrioventricular transition time has a minimum value, whereby the stimulation frequency found in this way is considered optimum for the respective degree of stress. What is also critical in this method is that the frequency changes in the search for the optimum simulation frequency result not only in a reaction of the heart muscle, but of the entire cardiovascular control system as well, whereby this reaction is a prerequisite for the desired optimization of the stimulation frequency.

EP-A-0 140 472 proposes the control of the stimulation frequency dependent on changes of the stroke volume of the heart, whereby these changes are identified with the assistance of impedance measurement. This publication, however, contains no teaching as to how the stroke volume can be quantified with the assistance of the measured values acquired from the impedance signal. It is also not recited how the individual differences of the proportionality between the value of the measured impedance signal and the degree of stress can be compensated.

DE-A-35 33 597 discloses a method wherein the stimulation frequency is regulated with a measured quantity proportional to the stroke volume. The control characteristic of the stimulation frequency as a function of the stroke volume is thereby independently identified in that the frequency is set given maximum stress such that the product of frequency and stroke volume becomes maximum. The disadvantage of this method is that the maximum stress condition must be detected by a second measured parameter, or must be externally input, and that no teaching is provided as to how the susceptibility of the impedance signal to disturbance is compensated, thus the method of this type has not enjoyed practical application.

SUMMARY OF THE INVENTION

An object of the invention, predominantly in combination with heart pacemakers, is to acquire measurement parameters of the heart activity such that they are free of noise signals and, thus, can be utilized for evaluating the physiological functions of the heart muscle, particularly for identifying changes of the cardiac time output.

According to the invention, an arrangement is provided, and particularly a heart pacemaker, which has a measuring means for acquiring a measurement parameter (M) of heart activity. A switch means is provided which, given a one-time or isolated change of frequency (F) or, respectively, duration ($t_S$) of a heart cycle (n+1) in comparison to a preceding heart cycle (n), evaluates a degree of a change of the measurement parameter (M) resulting from the change of frequency or duration. A control (9) varies the spacing between two successive stimulation pulses such that these variations which lead to an immediate reaction of the measurement parameter (M) are executed at such a spacing that a general pressure in a circulatory system does not change.

By contrast to the passive interference elimination methods such as frequency filtering previously used in pacemaker technology, a method of active interference blanking is applied here in order to suppress the influence of drift, sensitivity change, linearity change and multiple sensitivity. What is thereby fundamentally involved is to use designational modulation of only the phenomenon under investigation—for instance according to chronological criteria—to filter out the non-specific signal parts in the following demodulation. The pacemaker principle offers the best conditions for this purpose, since all measurement parameters of the heart activity depend on the frequency of the heart, and can thus be designationally modulated with the stimulation pulse.

The concept of the invention utilizes this fact in such a way that the signal curve of a measurement parameter M during a heart pulse n+1 is analyzed dependent on the frequency f or, respectively, duration $t_S$ of the preceding heart pulse n, and that, given a change of f by $\Delta f$ or, respectively, of $t_S$ by $\Delta t_S$, the measured value change $\Delta M$ between the measured values M(n) and M(n+1) is evaluated dependent on the degree of frequency change $\Delta f$ or, respectively $\Delta t_S$ between the two pulses, whereby measured value changes $\Delta M$ in the stimulation case that were produced by designational changes of the stimulation frequency f are analyzed.

When the dependency of a measurement parameter M on the degree of the frequency change $\Delta f$ is fundamentally physically exactly defined, all disturbing signal parts that are not dependent on the frequency change $\Delta f$ can be eliminated with the assistance of evaluation related to frequency change according to known, simple evaluation methods such as difference formation, quotient formation, and averaging.

For example, the physiological finding that changes of the pulse frequency, for instance due to shortening or lengthening of the pulse space $t_S$ between two stimulation pulses, can be utilized in order to effect an influencing of the diastolic filling phase of this heart pulse n and, thus, the curve of the systolic ejection phase during the next pulse n+1.

When the principle of signal evaluation related to frequency change is applied, for example, to the analysis of intracardial impedance measurements whose utilization was previously unsuccessful because of the high susceptibility of this measuring method to disruption, one succeeds in evaluating changes of the stroke volume which is so free of disturbance that, among other things, the stimulation frequency can be regulated in stress-dependent fashion with the assistance of the evaluated signals, and/or the stimulation frequency can be hemodynamically optimized with the assistance of the evaluated signals, and/or a tachycardia detection can be implemented with the assistance of the evaluated signals.

DESCRIPTION OF THE PREFERRED EMBODIMENTS

Figure 1:
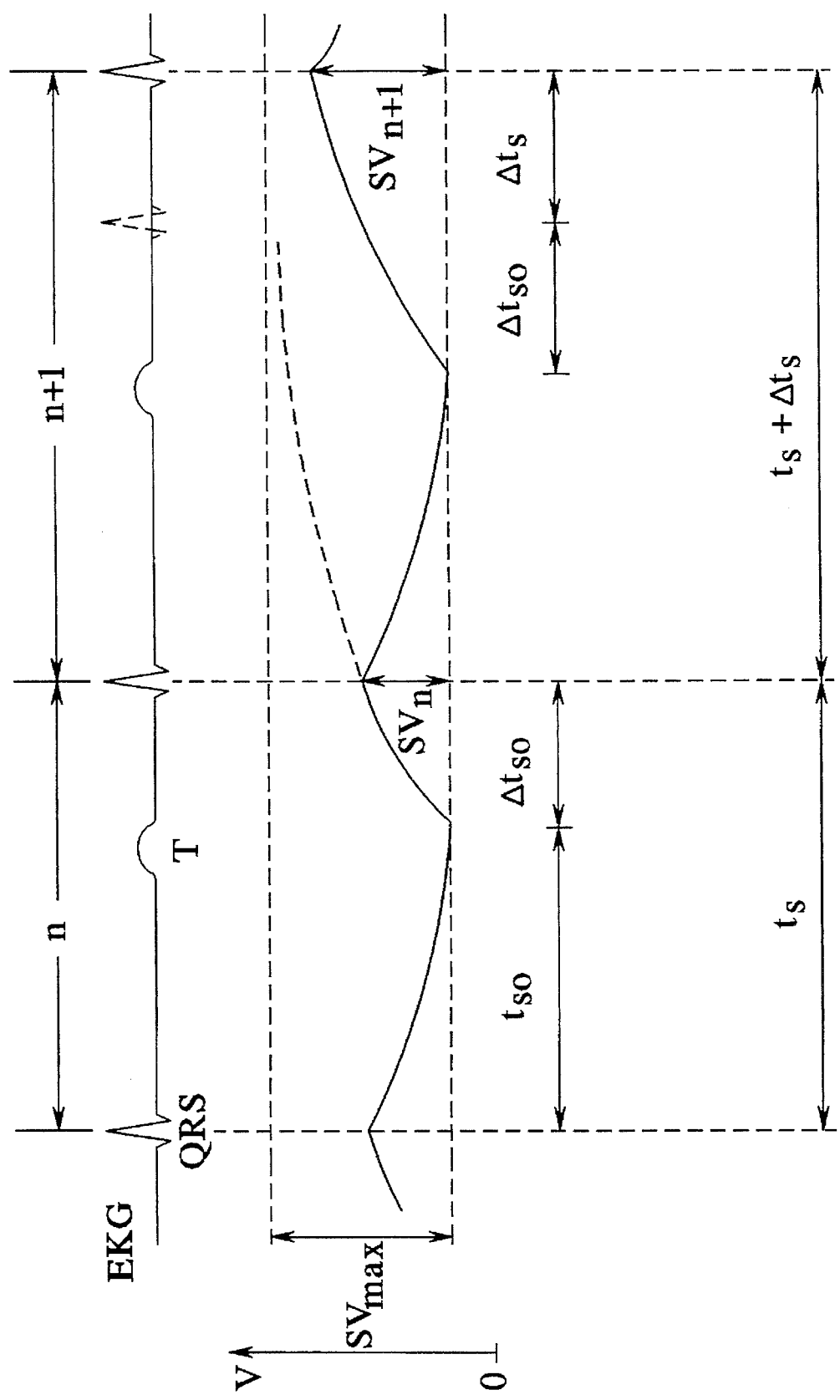
FIG. 1 is a curve of the electrocardiogram at the corresponding curve of the ventricle volume given a frequency change.

The upper part in FIG. 1 shows the signal curve of an electrocardiogram EKG over two successive heart cycles n and n+1 and, therebelow, shows the corresponding curve of the volume V of the two ventricles of a heart. The curve of the ventricle volume V is shown here, simplified by exponentially proceeding curve segments. The systolic phase wherein the heart muscle first tenses and subsequently contracts up to a residual volume, whereby the blood is ejected from the ventricles, begins upon appearance of the QRS complex in the EKG that initiates the heart cycle n. The length of the systolic phase is referenced $t_{SO}$ here. The diastolic phase wherein the ventricles relax and are subsequently refilled, given an exponentially proceeding enlargement of the ventricle volume V, begins at the end of the T-wave of the EKG. The length of the diastolic phase that is ended by the next-successive heartbeat is referenced $\Delta t_{SO}$, so that $t_S = t_{SO} + \Delta t_{SO}$ is valid for the duration $t_S$ of the heart cycle referenced n.

As FIG. 1 shows, the stroke volume $SV_n$ of the first heart cycle n can be approximately described by the equation $$SV_n = SV_{max} \cdot (1 - \exp(-\Delta t_{SO}/T))$$

whereby $SV_{max}$ is the stroke volume deriving on the basis of the given stress of the patient at a maximum duration of the heart cycle, and whereby T is the time constant—dependent on the contractibility of the heart muscle—for the rise of the ventricle volume V in the diastolic phase. Two parameters, namely $SV_{max}$ and T that change due to the change of the contractibility of the heart muscle dependent on the physical and psychic stress of the patient, enter into the above equation for the stroke volume $SV_n$. It is thus fundamentally possible to acquire the stress condition of the patient via a mensurational acquisition of the stroke volume SV such as, for example, the measurement of changes $\Delta Z$ of the electrical tissue impedance Z in the region of the heart and to utilize this, for example, for controlling the frequency of a heart pacemaker. It is thereby assumed that the impedance fluctuations $\Delta Z$ are proportional to the stroke volume SV. However, the measurement parameter dependent on the stroke volume, i.e. the impedance signal in this case, is subject to a plurality of disturbing influences such as, for example, the respiratory activity of the patient, motion artifacts, drift phenomena, sensitivity and linearity changes that do not correlate with the heart activity. As shall be disclosed below, the measurement parameter is evaluated dependent on the change of the duration of successive heart cycles n and n+1 for eliminating these disturbing influences.

As FIG. 1 shows, the duration of the heart cycle n+1 is lengthened by $\Delta t_S$ in comparison to the preceding cycle n, so that the diastolic phase of the second heart cycle n+1 is lengthened by the same amount $\Delta t_S$ given unmodified duration of the systole. Given an unvarying stress on the patient, $$SV_{n+1} = SV_{max} (1 - \exp(-(\Delta t_{SO} + \Delta t_S)/T))$$

thus derives for the stroke volume $SV_{n+1}$ of the second heart cycle n+1.

$$\Delta SV(+) = SV_{n+1} - SV_n = SV_{max} \exp(-(\Delta t_{SO}/T)) \cdot (1 - \exp(-\Delta t_S/T))$$

thus derives for the change $\Delta SV(+)$ of the stroke volume SV due to the enlargement of the spacing of successive heartbeats by the amount $+\Delta t_S$.

Given a shortening of the heart cycle duration, i.e. a change of the spacing between two heartbeats by $-\Delta t_S$, $$\Delta SV(-) = SV_{max} \exp(-(\Delta t_{SO}/T)) \cdot (1 - \exp(\Delta t_S/T))$$

correspondingly derives for the change $\Delta SV(-)$ of the stroke volume SV. The relationship of the two changes in stroke volume thus derives at $$\Delta SV(+)/\Delta SV(-) = -\exp(-\Delta t_S/T)$$

now only contains the stress-dependent time constant T without the disturbance-affected quantity $SV_{max}$.

Figure 2:
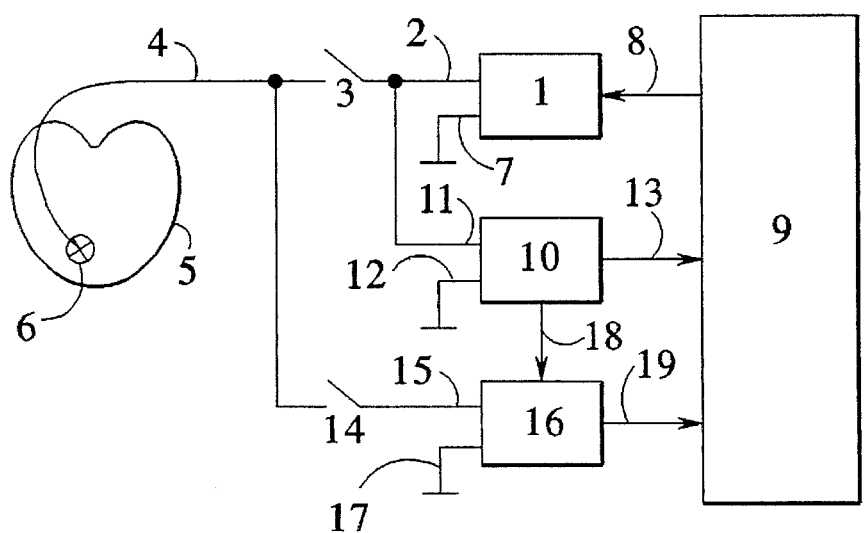
FIG. 2 is a block circuit diagram of a heart pacemaker, whereby a stress-dependent measurement parameter is acquired with the assistance of the frequency change, and is utilized for frequency control of the heart pacemaker.

FIG. 2 shows the block circuit diagram of a heart pacemaker wherein the above-described acquisition of a stress-dependent measurement parameter is utilized for controlling the stimulation frequency. The heart pacemaker contains a stimulation pulse generator 1 that has an output terminal 2 connected via a controllable switch 3 and via an electrode line 4 to an electrode 6 placed in the heart 5 of the patient. The second output terminal 7 of the stimulation pulse generator 1 is connected to the housing (not shown here) of the heart pacemaker, which serves as a reference electrode. The stimulation pulse generator 1 is connected via a control line 8 to a heart pacemaker control 9 that, via the control line 8, initiates the output of stimulation pulses by the stimulation pulse generator 1. A heartbeat detector 10 for the detection of stimulated or natural heartbeats is connected between the electrode 6 and the heart pacemaker housing. The detector 10 has a first input terminal 11 at the output terminal 2 of the stimulation pulse generator 1, and has a second input terminal 12 at the heart pacemaker housing. At its output side, the heartbeat detector 10 is connected to the heart pacemaker control 9 via a signal line 13. The electrode line 4 is connected via a further, controllable switch 14 to the first input terminal 15 of a measurement parameter pick-up unit 16 which, in the illustrated exemplary embodiment, acquires the tissue impedance between the electrode 6 and the heart pacemaker housing as a measurement parameter, the second input terminal 17 of the measurement parameter pick-up unit 16 being connected to the housing for this purpose. The measurement parameter pick-up unit 16 is connected to the heartbeat detector 10 via a control line 18 and is connected to the heart pacemaker control 9 via an output signal line 19. The controllable switches 3 and 14 serve the purpose of decoupling the stimulation pulse generator 1 and heartbeat detector 10 on the one hand and the measurement parameter pick-up unit 16 on the other hand, so that these cannot mutually influence one another. In the illustrated exemplary embodiment, the impedance measurement occurs between the electrode 6 and the heart pacemaker housing 17; however, a multi-electrode system is also conceivable wherein different electrodes are provided for the stimulation, heartbeat detection, and impedance measurement.

The functioning of the illustrated heart pacemaker is as follows. The heart pacemaker control 9 prescribes a defined frequency f that, for example, can be programmed proceeding from the outside, with which the stimulation pulse generator 1 is initiated to output stimulation pulses to the heart 5. The frequency f corresponds to the spacing $t_S$ of the individual stimulation pulses with $t_S=1/f$. Both natural as well as stimulated heartbeats are detected with the heartbeat detector 10. At every detected heartbeat, a time interval of the duration $t_S$ is started in the heart pacemaker control 9, the output of a stimulation pulse being initiated after the complete expiration thereof and the time interval being then restarted. When a natural heartbeat is detected before the expiration of this time interval, then the time interval is restarted without generating a stimulation pulse.

At the spacing of a plurality of seconds, the spacing between two successive stimulation pulses is alternately varied by the amount $+\Delta t_S$ and the amount $-\Delta t_S$ in the heart pacemaker control 9. These isolated changes each respectively lead to an immediate reaction of the stroke volume SV because of the change of the diastolic filling phase, whereas the general pressure in the circulatory system does not change and the average cardiac time output remains unvaried. The changes $\Delta SV(+)$ and $\Delta SV(-)$ of the stroke volume correspond to change $\Delta Z(+)$ and $\Delta Z(-)$ of the impedance fluctuations $\Delta Z$. The acquisition of the impedance with the measurement parameter pick-up unit 16 is synchronized with the detected heartbeats via the control line 18. Given a lengthening of the stimulation pulse spacing by $\Delta t_S$, thus the impedance fluctuation $\Delta Z_n$ is first acquired in the preceding heart cycle n and the impedance fluctuation $\Delta Z_{n+1}$ is subsequently acquired in the lengthened heart cycle n+1; subsequently, the difference between the two impedance fluctuations is formed with $\Delta(\Delta Z(+))=\Delta Z_{n+1}-\Delta Z_n$. The impedance fluctuation change $\Delta(\Delta Z(-))$ is calculated in the same way, given a shortening of the stimulation pulse spacing by $\Delta t_S$. The quotient $\Delta(\Delta Z(+))/\Delta(\Delta Z(-))$ is formed in the heart pacemaker control 9 with these two values, this quotient corresponding to the ratio of the stroke volume changes $\Delta SV(+)/\Delta SV(-)-\exp-(\Delta T_S/T)$ produced by the stimulation frequency change and, as already shown above, thus represents a measure for the stress condition of the patient. The actual value for the stress calculated in this way is compared to a rated value in the heart pacemaker control 9, this rated value being either capable of being prescribed as a constant value by an external programming unit which is not shown here, or is a matter of a value dependent on the frequency f. On the basis of the rated-to-actual value comparison, the frequency f with which the heart pacemaker control initiates the stimulation pulse generator 1 to output stimulation pulses is controlled.

An exemplary embodiment within the scope of the invention for hemodynamic frequency optimization in a heart pacemaker is set forth below with reference to FIG. 3 and FIG. 4. The internal circulation control of the body controls the cardiac time output HZV dependent on the physical and psychic stress of the patient. The cardiac time output HZV as a product of the heartbeat frequency f and the stroke volume SV is thereby dependent on the pressure difference $\Delta p$ and on the peripheral flow resistance R, i.e. $HZV=SV\cdot f=\Delta p/R$. The peripheral flow resistance R thereby reacts largely autonomously to the stress in that, for example upon activation of a muscle, the blood vessels thereof expand and thus effect a reduction of the peripheral flow resistance R. The brief-duration pressure drop caused as a result thereof is registered by corresponding receptors of the central nervous system and is converted into a signal to the heart muscle for increasing the cardiac time output HZV via the stroke volume SV and the heartbeat frequency f. The cardiac time output HZV then stabilizes on average to a value proportional to the stress.

Figure 3:
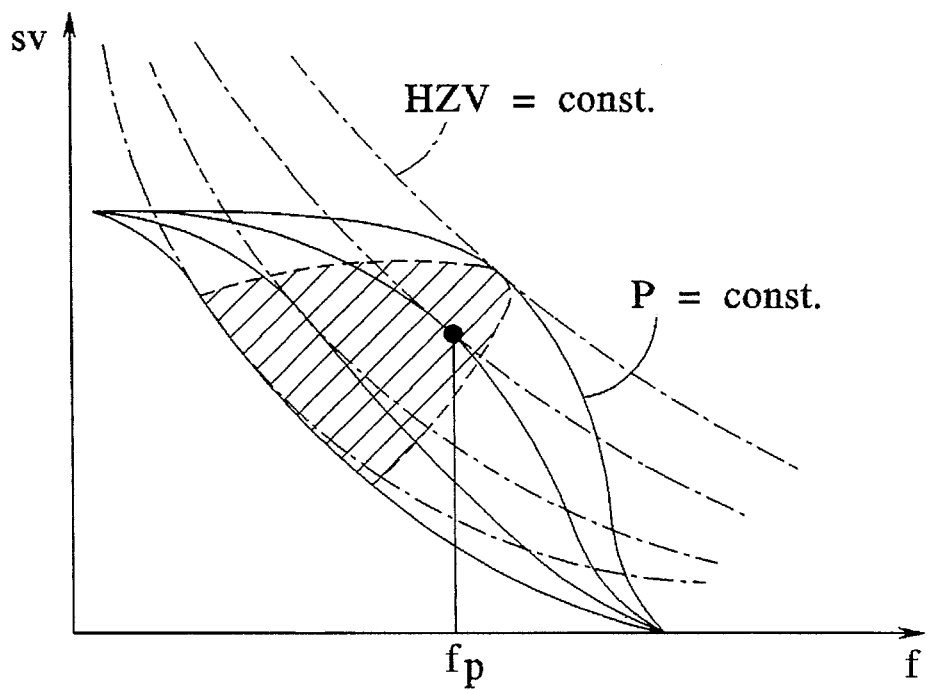
FIG. 3 is a diagram showing the curve of the stroke volume of a normal heart dependent on the heartbeat frequency given different levels of stress.

In a diagram for a normal heart, FIG. 3 shows the curve of the stroke volume SV dependent on the heartbeat frequency f given different stress levels P. The lines of constant cardiac time output HZV are entered with dot-dash lines. As the diagram shows, there is a frequency value $f_P$ for every stress condition P beginning with which a further increase in the heartbeat frequency f does not yield any further increase in the cardiac time output HZV. In the diagram, the region wherein a change of the frequency f yields practically no change of the cardiac time output HZV is entered in shaded fashion. The large scope of the individual fluctuation of the cardial conductivity makes it necessary for heart pacemaker patients to optimize the matching of the stimulation frequency to the stress situation such that the cardiac time output HZV proportionally adapts to the stress, and an increase in the frequency does not lead to a reduction in the cardiac time output HZV.

In a following explanation of an example for hemodynamic frequency optimization in a heart pacemaker, the above-recited finding is utilized to the effect that the internal circulation control of the body keeps the cardiac output HZV approximately constant, given an unchanging stress situation, in that increases $\Delta f$ in the stimulation frequency f are compensated by a corresponding reduction $-\Delta SV$ of the stroke volume SV beginning with a stress-dependent, individually typical value fp; i.e., $$HMV=SV\cdot f=(SV-\Delta SV)\cdot(f+\Delta f)$$

is valid for f greater than fp given constant stress. The relationship $$\Delta SV/SV=\Delta f/(f+\Delta f)$$

thus derives for the relative change of the stroke volume SV.

As FIG. 1 shows, shortenings of the pulse spacing $t_S$ by the amount $\Delta t_{SO}$ results in the stroke volume SV becoming zero in the second heart cycle n+1. What is then valid for the change $\Delta SV_O$ of the stroke volume SV is:

$$\Delta SV_o=SV_{n+1}-SV_n=O-SV_n$$

At a given stimulation frequency f, consequently the stroke volume SV can be identified in that the spacing between two stimulation pulses defining the heart cycle n+1 is shortened repeatedly by an amount $\Delta t_S$ that is greater every time in time intervals of a few seconds and the change $\Delta SV$ of the stroke volume SV produced as a result thereof are acquired. This procedure is continued as long as $\Delta SV$ thereby becomes greater. As soon as a value that is smaller in comparison to the preceding value is found for $\Delta SV$, however, the preceding, i.e. maximum value for $\Delta SV$ is defined as $\Delta SV_O=-SV_n$, and the amount $\Delta t_S$ by which the pulse spacing $t_S$ was shortened is defined as $\Delta t_{SO}$. As already shown in the preceding exemplary embodiment, the changes $\Delta SV$ or, respectively, $\Delta SV_O$ of the stroke volume SV, can be acquired via an impedance measurement in the region of the heart.

Since the impedance fluctuations $\Delta Z$ are a function of the stroke volume SV, the above-required identification of $\Delta SV/SV = -\Delta SV/\Delta_O$ can be identified on the basis of the ratio of the changes of the impedance fluctuations $\Delta(\Delta Z)/(\Delta Z_O)$, whereby $\Delta Z_O$ are the impedance fluctuations given a lengthening of the stimulation pulse space by $\Delta t_S = \Delta t_{SO}$.

Figure 4:
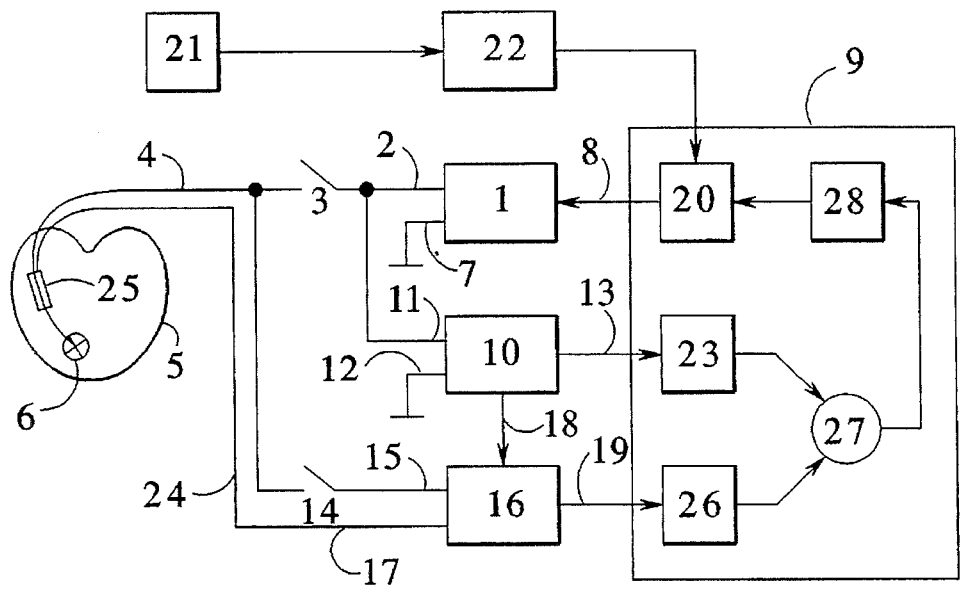
FIG. 4 is a block circuit diagram of a heart pacemaker having hemodynamic optimization of the stimulation frequency.

FIG. 4 shows the block circuit diagram of a heart pacemaker wherein the above-described, hemodynamic frequency optimization is applied; function blocks that are the same as in FIG. 2 are thereby provided with the same reference characters. The heart pacemaker contains a stimulation pulse generator 1 that has a first output terminal 2 connected via a controllable switch 3 and a first electrode line 4 to a distal point electrode 6 placed in the heart 5 of the patient. The second output terminal 7 of the stimulation pulse generator 1 is connected to the housing (not shown here) of the heart pacemaker. The stimulation pulse generator 1 is connected via a control line 8 to a frequency control unit 20 that is a component part of a heart pacemaker control 9 and controls the stimulation pulse generator 1 to output stimulation pulses with a prescribed frequency. The frequency is controllable dependent on the output signal of a sensor 21 that detects the stress condition of a patient, the output signal thereof being supplied via a signal evaluation means 22 to the frequency control unit 20. For detecting natural and stimulated heartbeats between the tip electrode 6 of the housing of the heart pacemaker, a heartbeat detector 10 has a first input terminal 11 connected to the output terminal 2 of the stimulation pulse generator 1 and has a second input terminal 12 connected to the heart pacemaker housing. At its output side, the heartbeat detector 10 is connected via a signal line 13 to a unit 23 for forming differences and quotients in the heart pacemaker control 9. A measurement parameter pick-up unit 16 has its first input terminal 15 connected via a further controllable switch 14 and the electrode line 4 to the point electrode 6, and has its second input terminal 17 connected via a second electrode line 24 to a ring electrode 25 that is spaced from the first electrode 6. The measurement parameter pick-up 16 serves the purpose of acquiring the impedance between the two electrodes 6 and 25. The measurement parameter pick-up unit 16 is also connected to the heartbeat detector 10 via a control line 18, and is connected to a signal handling unit 26 of the heart pacemaker control 9 via an output signal line 19. The unit 23 for forming differences and quotients and the signal handling unit 26 have their output sides connected to a difference comparator 27 whose output signal is supplied to a regulating unit 28 that controls the frequency control unit 20.

The frequency control unit 20 initiates the stimulation pulse generator 1 to output stimulation pulses with a frequency that is dependent on the stress condition of the patient acquired with a sensor. The spacing between two successive stimulation pulses is thereby shortened once by the amount $\Delta t_S$ in the spacing of a few seconds. At every such frequency change, the impedance in the heart 5 between the electrodes 6 and 25 is acquired in the measurement parameter pick-up unit 16 synchronously with the heartbeats detected by the heartbeat detector 10 and the difference $\Delta(\Delta Z)$ between the impedance fluctuations $\Delta Z_n$ in the heart cycle n preceding the change. The impedance fluctuations $\Delta Z_{n+1}$ in the heart cycle n+1 having the varied duration is formed in the signal handling unit 26. The event of the one-time reduction in pulse spacing is repeated with a greater and greater shortening $-\Delta t_S$ at the interval of a few seconds, and the respectively new value of $\Delta(\Delta Z)$ is compared to the previously calculated value in the signal handling unit 26. When the newly calculated value is greater than the preceding value, the procedure of reducing the pulse spacing is continued until the newly calculated value $\Delta(\Delta Z)$ is smaller by a prescribed amount than the previously calculated value. The previously calculated value of $\Delta(\Delta Z)$ is then defined as $\Delta(\Delta Z_O)$ and is stored.

When the frequency control unit 20 changes the stimulation frequency f over longer time intervals (minutes)— either because the sensor 21 detects a stress change or because the frequency control unit 20 is automatically implementing a frequency optimization—, then the new value of $\Delta(\Delta Z_O)_{m+1}$ caused as a result thereof is compared in the signal handling unit 26 to the value $\Delta(\Delta Z_O)_m$ most recently calculated before the longer—duration frequency change $\Delta f$ and the difference $\Delta(\Delta Z_O)$ between the two values is formed. Subsequently, the quotient $\Delta(\Delta(\Delta Z_O))/\Delta(\Delta Z_O)_m$ is formed, this corresponding to the relative change $\Delta SV/SV$ of the stroke volume SV due to the frequency change $\Delta f$. The quotient $\Delta f/(f+\Delta f)$ is formed in the unit 23 for forming differences and quotients, and is formed on the basis of the chronological appearance of the detected heartbeats. By comparing the output values of the function blocks 23 and 26, a decision is made in the difference comparator 27 as to whether the quotient $\Delta(\Delta(\Delta Z_O))/\Delta(\Delta Z_O)_m$, i.e. $\Delta SV/SV$, is greater than or smaller than the quotient $\Delta f/(f+\Delta f)$, and thus whether the frequency change $\Delta f$ has led to an improvement or deterioration of the cardiac time output $HMV = SV \cdot F$. Dependent on the result of the comparison, the frequency control unit 20 is controlled via the regulating unit 28 such that frequency changes $\Delta f$ that effect a deterioration of the cardiac time output HZV given constant stress are retracted.

Finally, an exemplary embodiment for recognizing tachycardial conditions of the heart shall be set forth below. Fundamentally, the efficiency of the heart muscle can be evaluated via the acquisition of the stroke volume SV and, specifically at high frequency f, a finding can be made as to whether the pulse actions of the heart muscle are ineffective, i.e. tachycardial. The analysis of measurement parameters depending on stroke volume with the assistance of short frequency changes by varying the pulse spacing of successive stimulation pulses enables the detection of such tachycardial conditions. Within the framework of the invention, the heartbeat frequency detected with the assistance of a heartbeat detector is modulated by brief frequency boosts $\Delta f_1, \Delta f_2, \ldots$, i.e. short reductions $\Delta t_{S1}, \Delta t_{S2} \ldots$ of the spacing $\Delta t_S$ of successive stimulation pulses, and an evaluation is carried out on the basis of forming differences and quotients to determine whether and to what extent the measurement parameter dependent on stroke volume has changed dependent on the frequency changes $\Delta f_1, \Delta f_2, \ldots$. When the change of the measurement parameter dependent on stroke volume lies below a prescribed threshold, then a tachycardial condition is detected and displayed.

An improved analysis can be achieved in that a change pattern of the measurement parameter dependent on stroke volume that is dependent on the changes $\Delta f_{11}, \Delta f_{12}, \ldots \Delta f_{21}, \Delta f_{22}, \ldots$ is produced for a plurality of high fundamental frequencies $f_1, f_2, \ldots$ is stored and is utilized for a comparative analysis for detecting a tachycardia.

Figure 5:
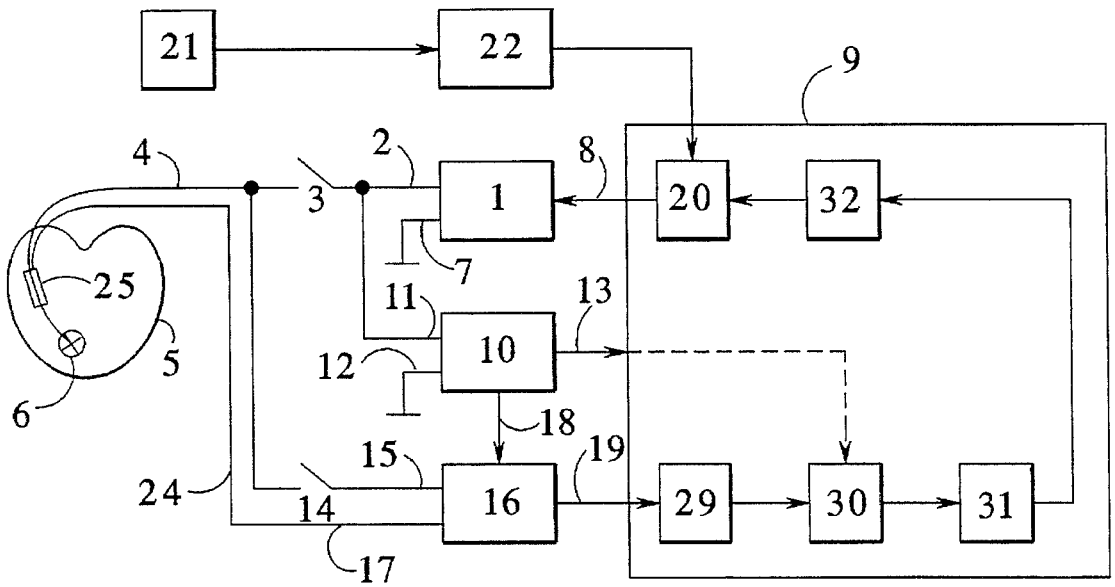
FIG. 5 is a block circuit diagram of a heart pacemaker having means for recognizing tachycardial conditions of the heart.

FIG. 5 shows a corresponding exemplary embodiment for the tachycardia detection in a heart pacemaker, whereby there are only differences in the structure of the heart pacemaker control 9 in comparison to the heart pacemaker shown in FIG. 4. The changes $\Delta(\Delta Z)$ of the impedance fluctuations $\Delta Z$ that have occurred due to the changes $\Delta t_S$ of the stimulation pulse spacing $t_S$ in two successive heart cycles n and n+1 are acquired in the evaluation circuit 29 following the measurement parameter pick-up 16, and the noise-affected quantity $SV_{max}$ is eliminated by quotient formation, just as in the exemplary embodiment of FIG. 2. The values thus determined are retained in a memory 30 which belong to the heartbeat frequency f detected by the heartbeat detector 10. The values stored in this way are compared to prescribed, programmable values or to a value pattern previously produced by the heart pacemaker. The comparisons are made in a further evaluation unit 31 for detecting a tachycardia. Upon detection of a tachycardia, a function unit 32 for controlling the frequency control unit 20 is activated for the purpose of ending the tachycardia.

Although various minor changes and modifications might be proposed by those skilled in the art, it will be understood that I wish to include within the claims of the patent warranted hereon all such changes and modifications as reasonably come within my contribution to the art.

I claim:

1. A heart pacemaker, comprising:

measuring means for acquiring a measurement parameter M of heart activity;

switch means for evaluating a degree of change of said measurement parameter M resulting from and dependent upon a degree of change of frequency f or duration $t_S$ of a heart cycle in comparison to a preceding heart cycle;

means for providing stimulation pulses;

control means for varying a spacing between two successive stimulation pulses such that 1) there is an immediate reaction of said measurement parameter M, and 2) a general pressure in a circulatory system associated with the heart does not change; and means for evaluating comprises means for calculating a quotient of two measurement parameter changes $\Delta M1$ and $\Delta M2$ that are measured dependent on different pulse spacing changes $\Delta t_{S1}$ and $\Delta t_{S2}$.

2. A heart pacemaker, comprising:

measuring means for acquiring a measurement parameter M of heart activity;

switch means for evaluating a degree of change of said measurement parameter M resulting from and dependent upon a degree of change of frequency f or duration $t_S$ of a heart cycle in comparison to a preceding heart cycle;

means for providing stimulation pulses;

control means for varying a spacing between two successive stimulation pulses such that 1) there is an immediate reaction of said measurement parameter M, and 2) a general pressure in a circulatory system associated with the heart does not change; and means for utilizing quotients of changes of stress-dependent measurement parameters for controlling the stimulation frequency based on a comparison to what is potentially a frequency-dependent rated value.

3. A heart pacemaker according to claim 2 including means for comparing a difference between two maximum measured value change values at two different fundamental frequencies f1 and f2, but at a same load with reference to a value $\Delta M_{max}$ at the frequency f1, to a quotient $\Delta f/(f+\Delta f)$; and means for utilizing said comparison value for hemodynamic optimization of frequency control.

4. A heart pacemaker, comprising:

measuring means for acquiring a measurement parameter M of heart activity;

switch means for evaluating a degree of change of said measurement parameter M resulting from and dependent upon a degree of change of frequency f or duration $t_S$ of a heart cycle in comparison to a preceding heart cycle;

means for providing stimulation pulses;

control means for varying a spacing between two successive stimulation pulses such that 1) there is an immediate reaction of said measurement parameter M, and 2) a general pressure in a circulatory system associated with the heart does not change; and means for evaluating difference values $\Delta M$ of a measured value M dependent on stroke volume given increasing value of frequency changes $\Delta f$ such that a maximum measured value change $\Delta M_{max}$ is detected at $\Delta f_O = 1/\Delta t_{SO}$.

5. A heart pacemaker, comprising:

measuring a means for acquiring a measurement parameter M of heart activity;

switch means for evaluating a degree of change of said measurement parameter M resulting from and dependent upon a degree of change of frequency f or duration $t_S$ of a heart cycle in comparison to a preceding heart cycle;

means for providing stimulation pulses;

control means for varying a spacing between two successive stimulation pulses such that 1) there is an immediate reaction of said measurement parameter M, and 2) a general pressure in a circulatory system associated with the heart does not change:

means for comparing quotients of various, brief changes of measurement parameters dependent on stroke volume at a same fundamental frequency to stored rated quotient values for this frequency; and means for analyzing efficiency of the heart muscle based on said comparisons for tachycardia detection.

6. A heart pacemaker, comprising:

measuring means for acquiring a measurement parameter M of heart activity;

switch means for evaluating a degree of change of said measurement parameter M resulting from and dependent upon a degree of change of frequency f or duration $t_S$ of a heart cycle in comparison to a preceding heart cycle;

means for providing stimulation pulses;

control means for varying a spacing between two successive stimulation pulses such that 1) there is an immediate reaction of said measurement parameter M, and 2) a general pressure in a circulatory system associated with the heart does not change;

means for comparing differences between brief-duration changes of frequency-dependent and stress-dependent measurement parameters during unchanging stress to moderate-duration changes of these parameters following a change in stress; and means for utilizing said comparisons for separating frequency-dependency of these parameters from the stress-dependency of these parameters.

* * * * *